United States Patent [19]

Gläser et al.

[11] 4,303,339

[45] Dec. 1, 1981

[54] GRAPHITE TUBE ASSEMBLY

[75] Inventors: Horst Gläser, Überlingen; Rolf Tamm, Salem, both of Fed. Rep. of Germany

[73] Assignee: Bodenseewerk Perkin-Elmer & Co., GmbH, Überlingen, Fed. Rep. of Germany

[21] Appl. No.: 154,727

[22] Filed: May 29, 1980

[30] Foreign Application Priority Data

Jun. 15, 1979 [DE] Fed. Rep. of Germany ....... 2924123

[51] Int. Cl.³ .......................................... G01N 21/74
[52] U.S. Cl. .................................... 356/244; 356/312
[58] Field of Search .............................. 356/312, 244

[56] References Cited

U.S. PATENT DOCUMENTS 4,111,563 9/1978 Tamm .............................. 356/244

OTHER PUBLICATIONS

English Translation of German Gebrauchsmuster 78 25 590, Nov. 30, 1978.

*Primary Examiner*—Vincent P. McGraw
*Attorney, Agent, or Firm*—S. A. Giarratana; E. T. Grimes; R. A. Hays

[57] ABSTRACT

A graphite tube assembly for use in the atomic absorption spectroscopic measurement of samples, particularly liquid samples, during the passage of a beam of radiation through a graphite tube is disclosed. The graphite tube assembly includes a graphite tube and a sample holding platform which are cooperatively adapted to allow the platform to be removed and reinserted, or exchanged with another platform, while maintaining a preselected orientation of the platform with respect to an inlet port extending through the wall of the graphite tube.

6 Claims, 2 Drawing Figures

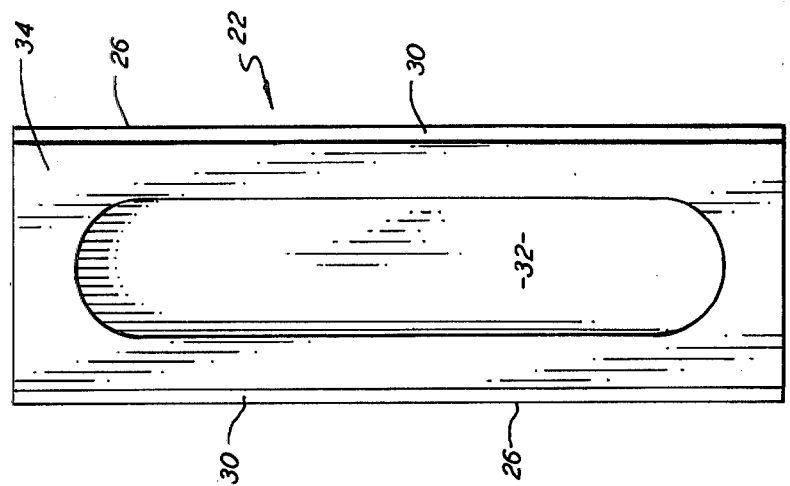
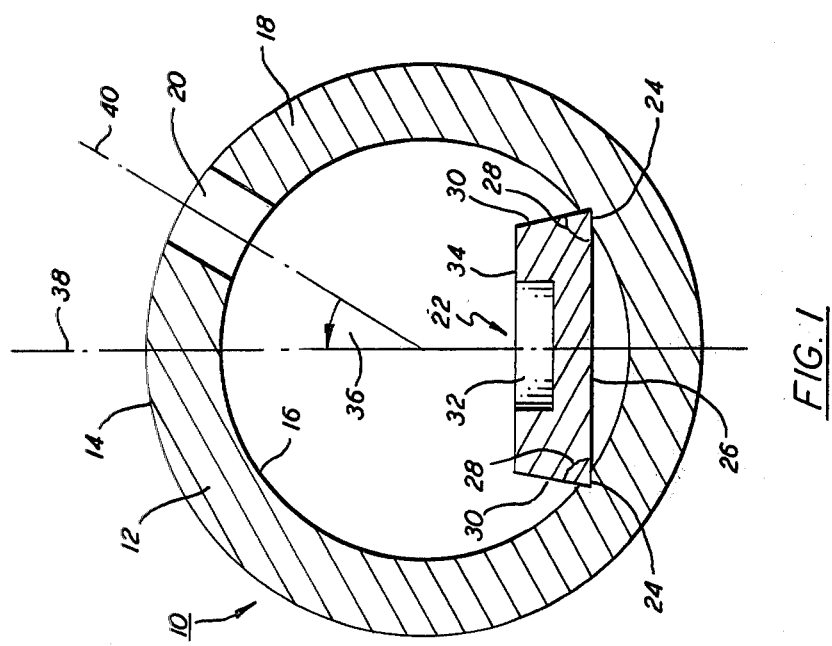

GRAPHITE TUBE ASSEMBLY

BACKGROUND OF THE INVENTION

The present invention generally relates to a graphite tube assembly for use in flameless atomic absorption spectroscopy and, in particular, relates to such a tube assembly adapted to cooperatively accept therein, at a preselected orientation, a sample holding platform.

During conventional atomic absorption spectroscopy measurements the graphite tube is placed in the path of a radiation beam and the sample to be measured is placed in a sample holding platform positioned within the tube but external to the path of the radiation beam. As well known the sample is then atomized and measurements are performed thereon. The sample to be tested is usually placed in the sample holding platform via an inlet port in the wall of the graphite tube.

It has been found, particularly when liquid samples are to be tested, that the sample holding platform is most advantageously oriented at a preselected angle from the center line of the inlet port. In addition, it has been found quite advantageous, in order to consistently achieve reliable results, to be able to exchange platforms, or remove and reinsert the same platform, while maintaining the same platform orientation with respect to the inlet port. That is, the preselected orientation should be the same for each platform inserted into the tube.

It is known, via U.S. Pat. No. 4,111,563, issued to Tamm, that the sample holding platform can be an integral portion of the graphite tube structure. While this may be advantageous to the maintenance of the preselected angle between the platform and the inlet port of the graphite tube, it has the disadvantage that the platform can not be exchanged or removed without destroying the graphite tube. Thus, if, for any reason, the sample holding platform has to be changed the arrangement in the above-referenced U.S. patent requires that the entire graphite tube be replaced.

SUMMARY OF THE INVENTION

In view of the art discussed above, it is a general object of this invention to overcome the non-interchangability of the sample holding platform while maintaining the ability to exactly position such a platform with respect to the inlet port of the graphite tube.

Another object of the present invention is to provide a graphite tube assembly in which the sample holding platform inserted therein is capable of withstanding external physical shocks such as those caused during the injection of a sample material.

In accordance with the present invention, the above objects are achieved by the use of a shaped platform having a sample receiving recess therein, which platform is adapted to mate with receptically adapted surfaces inside the graphite tube such that the platform is removable and repositionable, or exchangeable, to the same orientation within the graphite tube.

IN THE DRAWINGS

FIG. 1 is a cross-sectional view through a graphite tube assembly, not drawn to scale, embodying the principals of the present invention; and FIG. 2 is a plan view of a sample holding platform, not drawn to scale, embodying the principals of the present invention, for use with a graphite tube as shown in FIG. 1.

DETAILED DESCRIPTION OF A PREFERRED EMBODIMENT OF THE INVENTION

In a preferred embodiment of the invention, shown in FIG. 1, a graphite tube assembly, generally indicated at 10 in the drawing, includes a hollow graphite tube 12 having an outer cylindrical-like surface 14 and an inner cylindrical-like surface 16 concentric with the outer surface 14. The outer surface 14 and the inner surface 16 define a wall 18 having an inlet port 20 therethrough. The particular location of the inlet port 20 with respect to the periphery of the graphite tube 12 is more fully discussed below. As well known in the art, the tube 12 is arranged, or aligned, in the path of a radiation beam which passes therethrough for measuring the atomic absorption characteristics of a sample material. The graphite tube 12 also includes means for locating a sample holding platform 22 therein at a preselected orientation with respect to the inlet port 20. In this particular embodiment the orienting means is a pair of substantially parallel grooves 24 formed in the inner surface 16 of the graphite tube 12. The particular details of the grooves 24 are more fully discussed below.

In addition to the graphite tube 12, the assembly 10 includes the sample holding platform 22 having, in this embodiment, a generally trapezoidal cross-sectional shape. As shown, the trapezoidal platform 22 is contoured so that its comparatively wider surface 26, defining acute angles 28 with the sides 30 thereof, slidably mates with the grooves 24 formed in the inner surface 16 of the graphite tube 12. Hence, the platform 22 can be inserted into the tube 12, removed and reinserted, or exchanged with another platform having the same cross-sectional profile, without altering its orientation within the tube 12. As shown in FIG. 2, the sample holding platform 22 also includes a recess 32 in the comparatively narrower surface 34 thereof. The recess 32 is designed to hold quantities of test samples needed for the performance of flameless atomic absorption spectroscopy. For reasons well known in the art, the sample holding platform 22 is formed of a non-porous material.

It has been determined that the platform 22 should be oriented so that the offset angle 36, which is here defined as the acute angle between a line 38 normal to the comparatively narrower surface 34 and a line 40 axially through the inlet port 20, is on the order of about 27 degrees. The 27 degree offset angle 36 has been determined to be the most advantageous to permit the insertion of liquid samples through the inlet port 20 into the graphite tube 12. In fact, this is particularly advantageous when a pipette, not shown, is inserted through the inlet port 20 to dispense the liquid sample into the recess 32. A further advantage, in addition to the repeatability of the orientation of the platform 22, the mating surfaces as described above firmly hold the platform in a fixed position. Thus the assembly 10 can survive, without change in platform orientation, external physical shocks which may impinge upon the graphite tube 12.

It has thus been shown that the present invention does indeed provide a novel graphite tube assembly for use in an atomic absorption spectrometer. While the invention has been described herein with particular reference to a specific preferred embodiment thereof it will be understood by those skilled in the art that various changes and modifications can be made without departing from the spirit and scope of the invention as defined by the claims appended hereto.

What is claimed is:

1. A graphite tube assembly for use in an atomic absorption spectrometer comprising:
    a graphite tube adapted to permit a radiation beam to be transmitted therethrough, said tube having an inlet port extending through a wall thereof; and
    a sample holding platform having a recess in one surface thereof for retaining a sample material to be tested, said sample holding platform being adapted to be disposed within said graphite tube external of said beam path, said platform and said tube having, cooperatively mating surfaces for locating said platform at a preselected orientation within said tube whereby said platform can be removed and reinserted, or exchanged with another similarly shaped platform, to said preselected orientation.

2. A graphite tube assembly as claimed in claim 1 wherein said platform has a trapezoidal cross-section having a comparatively narrower surface and a comparatively wider surface, said comparatively wider surface being spaced apart from said comparatively narrower surface by a pair of side surfaces which define acute angles with said comparatively wider surface.

3. A graphite tube assembly as claimed in claim 2 wherein said graphite tube includes a pair of grooves adapted to receive said platform, said grooves mate with said acute angles defined by said side surfaces and said comparatively wider surface.

4. A graphite tube assembly as claimed in claim 2 wherein said platform is so oriented that an imaginary line normal to said comparatively narrower surface defines an acute angle with an imaginary line extending axially through said inlet port.

5. A graphite tube assembly as claimed in claim 4 wherein said acute angle is about 27 degrees.

6. A graphite tube assembly as claimed in claim 2 wherein said comparatively narrower surface of said platform includes said recess.

* * * * *